United States Patent

Wang (10) Patent No.: US 12,027,270 B2
(45) Date of Patent: Jul. 2, 2024

(54) METHOD OF TRAINING MODEL FOR IDENTIFICATION OF DISEASE, ELECTRONIC DEVICE USING METHOD, AND NON-TRANSITORY STORAGE MEDIUM

(71) Applicant: Fulian Precision Electronics (Tianjin) Co., LTD., Tianjin (CN)

(72) Inventor: Yu-Jen Wang, Taipei (TW)

(73) Assignee: Fulian Precision Electronics (Tianjin) Co., LTD., Tianjin (CN)

( * ) Notice: Subject to any disclaimer, the term of this patent is extended or adjusted under 35 U.S.C. 154(b) by 374 days.

(21) Appl. No.: 17/538,025

(22) Filed: Nov. 30, 2021

(65) Prior Publication Data

US 2022/0415504 A1    Dec. 29, 2022

(30) Foreign Application Priority Data

Jun. 29, 2021 (CN) .......................... 202110724665.7

(51) Int. Cl.
*G16H 50/20* (2018.01)
*G06N 3/08* (2023.01)
(Continued)

(52) U.S. Cl.
CPC .............. *G16H 50/20* (2018.01); *G06N 3/08* (2013.01); *G06T 7/0012* (2013.01); *G06V 10/98* (2022.01);
(Continued)

(58) Field of Classification Search
CPC ........ G16H 50/20; G16H 30/20; G16H 30/40; G16H 50/50; G06N 3/08; G06N 3/048; G06N 3/045; G06N 3/0464; G06T 7/0012; G06T 2207/20081; G06T 2207/10024; G06T 2207/20084; G06V 10/98; G06V 10/82; Y02A 90/10

See application file for complete search history.

(56) References Cited

U.S. PATENT DOCUMENTS 11,880,982 B2 *   1/2024  Ma ........................ G06T 7/174
2021/0319561 A1 * 10/2021  Fang ....................... G06T 7/11
(Continued)

OTHER PUBLICATIONS

A multiscale residual pyramid attention network for medical image fusion Author: Jun Fu, Weisheng Li, Jiao Du, Yuping Huang Publication: Biomedical Signal Processing and Control Apr. 2021 (Year: 2021).*

(Continued)

*Primary Examiner* — Santiago Garcia
(74) *Attorney, Agent, or Firm* — ScienBiziP, P.C.

(57) ABSTRACT

A method training an AI model in disease identification establishes a disease identifying model, the model includes a convolutional neural network and a pyramid attention network. The pyramid attention network receives output of the convolutional neural network. The method obtains feature map sample set, the sample set being classified into training sets and verification sets. The method inputs each training set into the disease identifying model to train the model and outputs values of degree of confidence in correct identification of diseases. The method further verifies the trained models according to the verification sets. An electronic device and a non-transitory storage medium are also disclosed.

14 Claims, 5 Drawing Sheets

(51) Int. Cl.
  *G06T 7/00*   (2017.01)
  *G06V 10/98*  (2022.01)
  *G16H 30/20*  (2018.01)

(52) U.S. Cl.
  CPC ... *G16H 30/20* (2018.01); *G06T 2207/20081* (2013.01)

(56) References Cited

U.S. PATENT DOCUMENTS

| | | | | |
|---|---|---|---|---|
| 2022/0067936 | A1* | 3/2022 | Lee | G06N 3/045 |
| 2022/0092755 | A1* | 3/2022 | Lyu | G06T 5/00 |
| 2022/0104474 | A1* | 4/2022 | Chellappan | H04R 1/08 |
| 2023/0018494 | A1* | 1/2023 | Gribble | A61B 5/4076 |
| 2023/0104945 | A1* | 4/2023 | Mao | G06T 7/0012 |
| | | | | 382/128 |
| 2023/0136558 | A1* | 5/2023 | Hawkins | A61B 34/25 |
| | | | | 382/128 |
| 2023/0186659 | A1* | 6/2023 | Martin | G06V 10/454 |
| | | | | 382/133 |
| 2023/0215063 | A1* | 7/2023 | Gadiyar | G06V 10/751 |
| | | | | 382/128 |
| 2023/0290480 | A1* | 9/2023 | Bose | A61N 5/1039 |
| 2023/0337636 | A1* | 10/2023 | Shmigelsky | G06V 40/10 |
| 2023/0368381 | A1* | 11/2023 | Savvides | G06V 10/774 |
| 2024/0005508 | A1* | 1/2024 | Zhang | G06T 7/0012 |

OTHER PUBLICATIONS

Sertan Serte et al., Deep learning for diagnosis of COVID-19 using 3D CT scans, Computers in biology and medicine 132 (2021) 104306, Mar. 10, 2021, pp. 1-8.

Manuel Vazquez Enriquez, A Deep Learning Approach for Pneumonia Detection in Chest X-Ray, Telecommunications Engineering School, 2019, pp. 1-85.

Saeid Asgari Taghanaki et al., Deep Semantic Segmentation of Natural and Medical Images: A Review, Artificial Intelligence Review, Jun. 13, 2020, pp. 1-45.

* cited by examiner

METHOD OF TRAINING MODEL FOR IDENTIFICATION OF DISEASE, ELECTRONIC DEVICE USING METHOD, AND NON-TRANSITORY STORAGE MEDIUM

FIELD

The subject matter herein generally relates to AI in medical technology, to use of medical images, and particularly to a method of training disease identifying model, an electronic device applying the method, and a non-transitory storage medium.

BACKGROUND

Images for medical purposes have become indispensable in modern medical diagnosis. The subtlety of features of diseases may be easily overlooked during identification by human medical staff, so artificial intelligence is used more and more to identify what is being portrayed in medical images. However, accuracy of identification based on artificial intelligence is lower and the adaptations need to be improved.

SUMMARY

An embodiment of the present application provides a method for training disease identifying model, an electronic device applying the method, and a non-transitory storage medium, which is capable of obtaining a trained disease identifying model with a more suitable adaptation and a higher accuracy.

An embodiment of the present application provides a method of training in identification of disease by establishing a disease identifying model. The disease identifying model includes a convolutional neural network and a pyramid attention network. The pyramid attention network is connected to an output of the convolutional neural network. The method obtains feature map sample set. The feature map sample set are classified into one or more training sets and one or more verification sets. The method inputs each of the training sets into the disease identifying model to train the disease identifying model according to the one or more training sets and outputs values of degree of confidence in correct identification of disease ("confidence values"). The method further verifies the disease identifying models after being trained according to the one or more verification sets and the confidence values.

According to some embodiments of the present application, the obtaining of a feature map sample set includes, obtaining a preset number of the medical images, and preprocessing the obtained preset number of the medical images to obtain the feature map sample set.

According to some embodiments of the present application, the preprocessing of the obtained preset number of the medical images to obtain the feature map sample set includes resampling the medical images, converting the medical images after resampling to three-dimensional RGB images, and converting the three-dimensional RGB images into the feature maps of the medical images.

According to some embodiments of the present application, the converting of the three-dimensional RGB images into the feature maps of the medical images includes mean normalization of the converted three-dimensional RGB images, and performing image enhancement on the three-dimensional RGB image after the mean normalization, to convert to the feature maps of the medical images.

According to some embodiments of the present application, the establishing of the disease identifying model includes selecting one convolutional neural network, and selecting one pyramid attention network. The disease identifying model includes the convolutional neural network and the pyramid attention network if the pyramid attention network needs to be used in the disease identifying model. The confidence values are output via the pyramid attention network.

According to some embodiments of the present application, the method further outputs the confidence values via a preset function of the convolutional neural network if the pyramid attention network does not need to be used in the disease identifying model.

According to some embodiments of the present application, the method further determines whether the confidence value is greater than a preset threshold, and outputs the disease corresponding to the confidence value if the confidence value is greater than the preset threshold.

An embodiment of the present application also provides an electronic device. The electronic device includes a storage device, and at least one processor. The storage device stores one or more programs, which when executed by the at least one processor, cause the at least one processor to establish a disease identifying model. The disease identifying model includes a convolutional neural network and a pyramid attention network. The pyramid attention network is connected to an output of the convolutional neural network. The at least one processor obtains feature map sample set. The feature map sample set are classified into one or more training sets and one or more verification sets. The at least one processor inputs each of the training sets into the disease identifying model to train the disease identifying model according to the one or more training sets and output confidence values. The at least one processor further verifies the disease identifying models after being trained according to the one or more verification sets and the confidence values.

An embodiment of the present application also provides a non-transitory storage unit. The non-transitory storage medium stores a set of commands, the commands being executed by at least one processor of an electronic device enable the at least one processor to establish a disease identifying model. The disease identifying model includes a convolutional neural network and a pyramid attention network. The pyramid attention network is connected to an output of the convolutional neural network. The at least one processor is caused to obtain feature map sample set. The feature map sample set are classified into one or more training sets and one or more verification sets. The at least one processor inputs each of the training sets into the disease identifying model to train the disease identifying model according to the one or more training sets and outputs confidence values. The at least one processor further verifies the disease identifying models after being training according to the one or more verification sets and the confidence values.

A method of training a model for disease identification, an electronic device, and a storage medium capable of applying the training with different specifications are disclosed, and accordingly the trained disease identifying module can be adapted to different medical images and provides a higher recognition rate.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Implementations of the disclosure will now be described, by way of embodiments only, with reference to the drawings. The disclosure is illustrative only, and changes may be made in the detail within the principles of the present disclosure. It will, therefore, be appreciated that the embodiments may be modified within the scope of the claims.

In addition, it should be understood that in the description of this application, terms such as "first" and "second" are used only for distinguishing in the description, but are not intended to indicate or imply relative importance or an order. The terms "exemplary" and/or "example" are used herein to mean "serving as an example, instance, or illustration." Any embodiment described herein as "exemplary" and/or "example" is not necessarily to be construed as preferred or advantageous over other embodiments. A feature that limited by "first", "second" may expressly or implicitly include at least one of the features. Use of the word exemplary is intended to present concepts and techniques in a concrete fashion.

Figure 1:
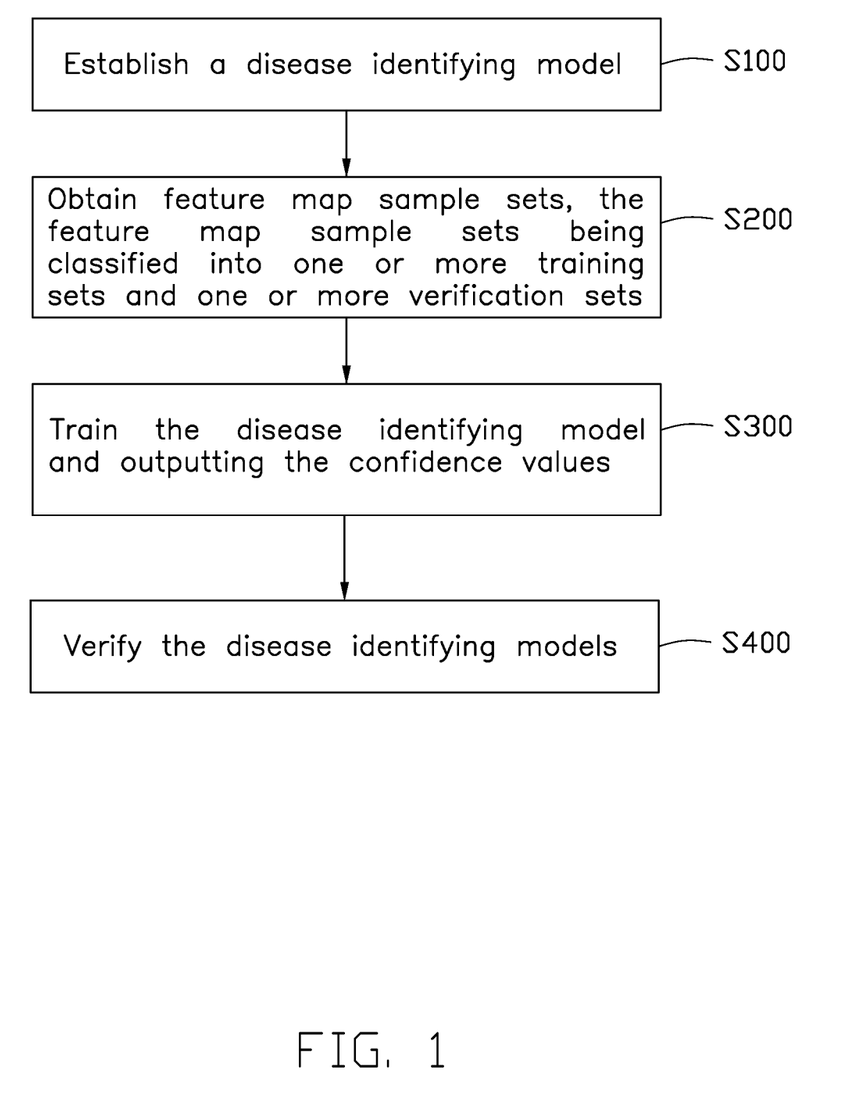
FIG. 1 is a flowchart of an embodiment of a method of training a model for disease identification.

FIG. 1 is a flowchart of an embodiment of a method of training disease identifying model. As shown in the FIG. 1, the method of training disease identifying model at least includes:

At step S100, establishing a disease identifying model.

In some embodiments, establishing the disease identifying model is based on a convolutional neural network (CNN) and a pyramid attention network. The pyramid attention network is connected to an output of the CNN.

It can be understood that, an attention mechanism is one CNN which is capable of using limited attention to quickly screen high-value information from a large amount of information. The pyramid attention network is an attention mechanism. The attention mechanism can be used to augment one layer of the CNN. However, when using the pyramid attention network, the pyramid attention network can use each level of the pyramid of the attention mechanism.

In some embodiments, an input of the disease identifying model is medical images which are pre-processed, namely feature maps. An output of the disease identifying model is one or more confidence values. Each confidence value represents a similarity between image feature of the image and the image feature in a disease state. The confidence value can be set as a number in a range of 0 to 100. A higher value of the number represents a higher degree of similarity.

In some embodiments, the disease identifying model is configured to determine whether one or more image features correspond to any disease existing or portrayed in the medical image. The disease identifying model can simultaneously identify many diseases and output the confidence value corresponding to each disease.

In some embodiments, a threshold judgement is arranged at an output of the disease identifying model. For example, if the confidence value is greater than a threshold, the disease identifying model outputs the corresponding disease. The threshold can be set according to the confidence value. For example, when the confidence value as to a particular disease is a number in a range of 0 to 100, the threshold can be set to 60, namely, when the confidence value of such disease is greater than 60, the disease identifying model outputs the disease.

In some embodiments, the threshold can be calculated by reference to accuracy rate, recall rate, and F1 value. Accuracy rate is a percentage of correct predictions among the total samples. Recall rate is a probability of true positive samples being predicated as positive samples. F1 value is a precision-recall curve. The negative relationship between the precision rate and the recall rate means that a high precision value and a high recall value cannot be achieved simultaneously, and the F1 value weighs the precision rate and the recall rate in a balanced way, enabling the precision rate and the recall rate to both achieve a perfect value simultaneously.

In some embodiments, the number of the diseases can be zero, indicating that no disease can be identified from the medical image. Although the number of the diseases can be zero, N is a positive integer which is greater than zero, representing that the number of the diseases identified from a medical image can be N.

At step S200, obtaining feature map sample set, the feature map sample set being classified into one or more training sets and corresponding verification sets.

It can be understood that, in some embodiments, each training set can be used to train the disease identifying model, and each verification set can be used to verify effectiveness of the disease identifying model.

It can be understood that, the number of feature maps of each training set can be greater than the number of feature maps of the verification set. For example, a ratio of feature maps of each training set to the feature maps of corresponding verification set can be three to one, or four to one.

In some embodiments, the feature map sample set can be obtained in the following manner:

Firstly, a preset number of the medical images are obtained.

In some embodiments, the medical images can include, but are not limited to, x-ray film, computed tomography, magnetic resonance, ultrasound inspection image, nuclear medicine image, and so on. Obviously, the method of the disclosure can train the model according to the medical images from different resources.

Secondly, the preset number of the obtained medical images are preprocessed to obtain the feature map sample set.

In some embodiments, the medical images can originate from different types of scanning devices. The medical images can be different specifications, different parameters, and different contrasts. Thus, a preprocessing of the medical images is needed to obtain feature maps of the images with a uniform specification.

It can be understood that, the images with the uniform specification obtained after the preprocessing can be feature maps. Thus, the feature maps of the images with the uniform specification form the feature map sample set. The feature maps in the feature map sample set are classified into the training set and the verification set. The feature maps in the training set are used to train the disease identifying model, and the feature maps in the verification set are used to verify effectiveness of the disease identifying model.

It can be understood that, the medical images being converted into the feature maps means that the disease identifying model can be trained according to the feature maps with a fixed format. The parameters of the images input into the disease identifying model do not need to be adjusted. Thus, the method of the disclosure improves a speed of training of the disease identifying model and an accuracy of identifying disease via the preprocessing of the images.

It can be understood that, in some embodiments, the feature maps of the medical images can be stored in 32-bit floating point formats. Floating point numbers can be represented in exponential manner. Each floating point number includes number sign bit, mantissa bits, exponent sign bit, and exponent bits. The number sign bit is a one-bit binary number which represents the sign of the number, for example, positive or negative. The exponent sign bit is a one-bit binary number which represents the sign of the exponent, for example, positive or negative. The mantissa bits are the significand of the floating point number. The exponent bits are the significand of the exponent.

Figure 2:
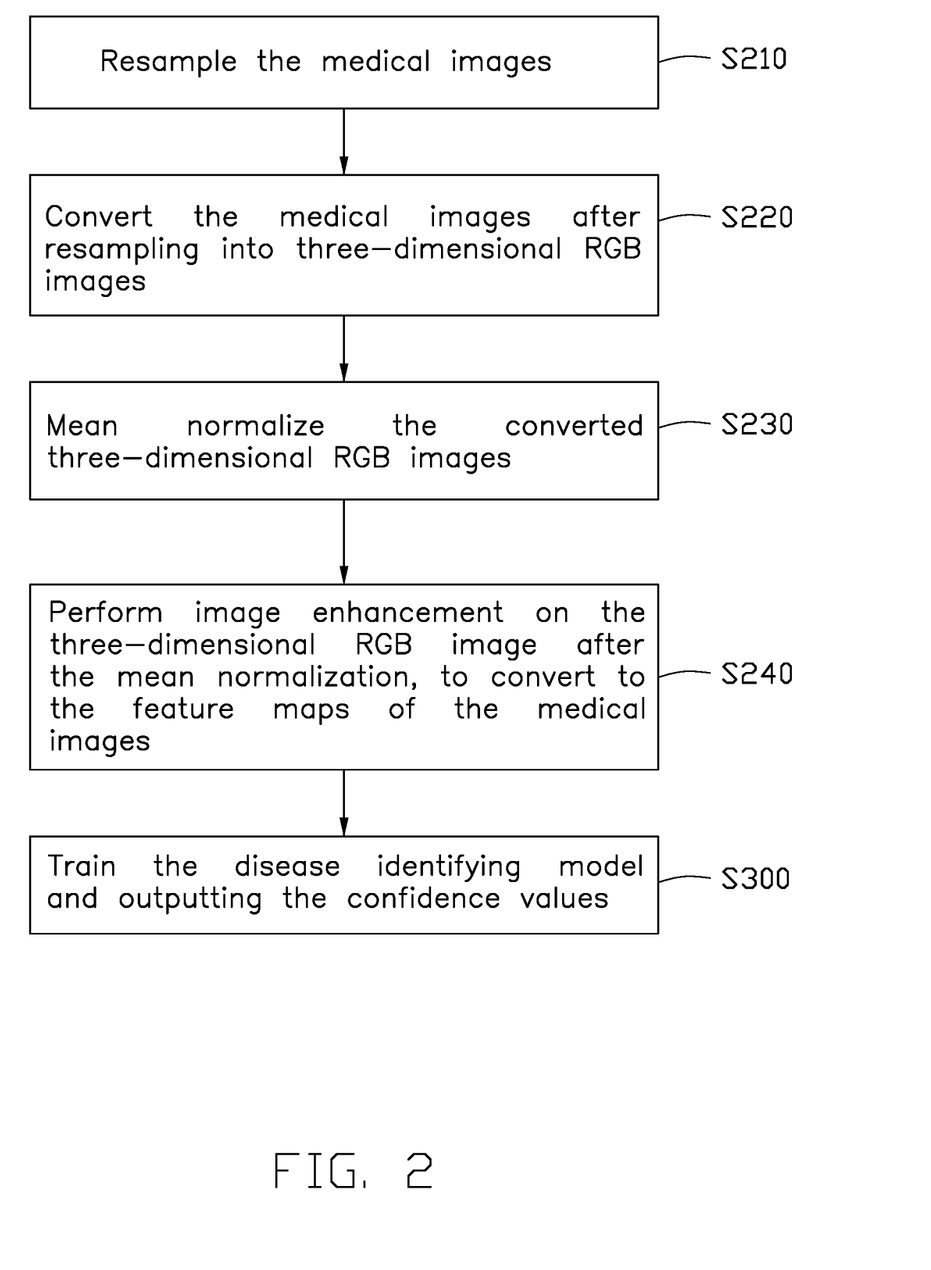
FIG. 2 is flowchart view of a process for preprocessing an obtained preset number of medical images in the method.

Referring also to FIG. 2, a process for preprocessing a preset number of obtained medical images in the method includes:

At step S210, resampling the medical images.

In some embodiments, resampling the medical images can adjust sizes of the medical images to obtain medical images with a uniform size. The resampling can include an upsampling and a downsampling. The upsampling can resize the image upwards, the downsampling can resize the image downward.

At step S220, converting the medical images after resampling into three-dimensional RGB images.

In some embodiments, each three-dimensional RGB image is a three-dimensional matrix made up of height, width, and channel corresponding to the three-dimensional RGB image. For example, a three-dimensional RGB image of size 6*6*3 represents the height of the three-dimensional RGB image as 6, the width of the three-dimensional RGB image as 6, and the channel of the three-dimensional RGB image as 3. During the operation, the RGB and a filter can have same number of channels.

It can be understood that, in some embodiments, a function in the language, for example, Python, Java, Matlab, and the like, can convert the medical images into the three-dimensional RGB images, the disclosure is not limited herein.

At step S230, mean normalizing the converted three-dimensional RGB images.

In some embodiments, the feature value of each three-dimensional RGB image can be mapped to a range of 0 to 1 or −1 to 1, thus the three-dimensional RGB images are normalized according to their mean.

It can be understood that, after the mean normalization, the optimizing process of an optimal solution becomes slower, converging to the optimal solution correctly is more convenient.

In some embodiments, after the step S230, the method further includes flipping the three-dimensional RGB image. It can be understood that, the flipping of the three-dimensional RGB image improves variety of the images. For example, when the number of the medical images in the obtained feature map sample set are insufficient, the three-dimensional RGB images can be flipped to increase the number of images used for training, thus a training effect of the disease identifying model can be improved.

At step S240, performing image enhancement on the three-dimensional RGB image after the mean normalization, to convert to the feature maps of the medical images.

In some embodiments, the manner of image enhancement can include, but is not limited to, Gaussian filter, de-blurring, sharpness, adjusting shade, and improving contrast, and so on. The manner of image enhancement can be set according to defect of each three-dimensional RGB image. For example, if in the three-dimensional RGB image the gaussian nose exists, a Gaussian filter can be used as a weighted average of the whole image. Namely, in the three-dimensional RGB image output via Gaussian filter, the value of each pixel is a weighted average of the pixel and the neighborhood around the pixel. It can be understood that, performing Gaussian filtration on the three-dimensional RGB image can reduce the gaussian noise in the three-dimensional RGB image and improve a definition of the three-dimensional RGB image.

At step S300, training the disease identifying model and outputting the confidence values.

In some embodiments, the training set and the verification set can be reclassified before training, namely the feature map sample set is classified into training sets and verification sets before training. During each training, one training set can thus be used to train the disease identifying model to form one disease identifying model after being trained. In some embodiments, the training set and the verification set can be reclassified after each training, namely the feature map sample set is classified into a training set and a verification set before training and is reclassified into one or more training sets and one or more verification sets during training, thus the reclassified training set can be used to train the disease identifying model again to form one disease identifying model after being trained.

In some embodiments, the feature maps of the training set and the feature maps of the verification set can be varied to form many training sets and many verification sets. In some embodiments, the feature map sample set can be reclassified to form many training sets and corresponding verification sets, for example, the feature map sample set can include a sample 1, a sample 2, a sample 3, and a sample 4. The sample 1, the sample 2, and the sample 3 can be classified in the training set 1, and the sample 4 can be classified in the verification set 1. The sample 1, the sample 2, and the sample 4 can be reclassified in the training set 2, and the sample 3 can be classified in the verification set 2.

In some embodiments, the feature map sample set can be flipped and the feature map sample set after being flipped can be reclassified to form many training sets and verification sets.

In some embodiments, the feature maps in each training set are input into the disease identifying model to train the disease identifying model, and accordingly a disease identifying model after being trained is formed.

It can be understood that, for example, the number of training samples in one embodiment is 1000, the total number of the training samples present in a single training, namely batch size, is 100, and the iterations training all the samples, namely the epoch, is 100, thus one batch size of samples is input into the model each time to obtain the confidence value, and 100 iterations are needed to complete one epoch.

It can be understood that, after the all epoch cycles have been completed, the method further performs a statistics to the output confidence values and the corresponding disease identifying models, for verification and analysis the disease identifying models.

At step S400, verifying the disease identifying models after being trained.

In some embodiments, the disease identifying models are verified via the values of degree of confidence in correct identification of diseases and the verification sets.

In some embodiments, the disease identifying models are verified via the feature maps in the verification sets and a preset classifier. In some embodiments, the disease identifying models are verified via the values of degree of confidence in correct identification of diseases, the verification sets, and a preset classifier. The classifier can use a received operating characteristic (ROC) curve, an accuracy of identifying the disease, or a loss of the correct information to verify the disease identifying models.

In some embodiments, after obtaining the disease identifying models verified after many verification cycles of the step S400, the method further sifts the disease identifying models according to the verification, and retains a disease identifying model with a higher rate of identification, for example, retaining a disease identifying model with a greater area underneath the ROC curve (AUC). The ROC curve represents evaluation sensitivities on a same signal. AUC value can be used to intuitively assess the quality of the classifier. A larger AUE value indicates a better performance of the classifier.

In some embodiments, a disease identifying model with the highest accuracy will be retained.

In some embodiments, a disease identifying model with the lowest loss of correct information will be retained.

In some embodiments, the disease identifying module can extract feature of the pulmonary disease in the x-ray film, thus different pulmonary diseases which may appear in the x-ray film can be identified.

In some embodiments, after completing the sifting of the disease identifying model, the trained disease identifying model is obtained. Thus, when the trained disease identifying model is used in diagnosis of diseases, a pre-diagnosed medical image is directly input into the disease identifying model, to output a diagnosis according to the trained disease identifying model and further output one or more confidence values in relation to the one or more diseases.

It can be understood that, the disease identifying model can use a class activation map and the confidence value to generate a power map of a category of the disease. It can be understood that, the power map of the category of the disease can be used to directly inspect the categories of a variety of diseases.

Figure 3:
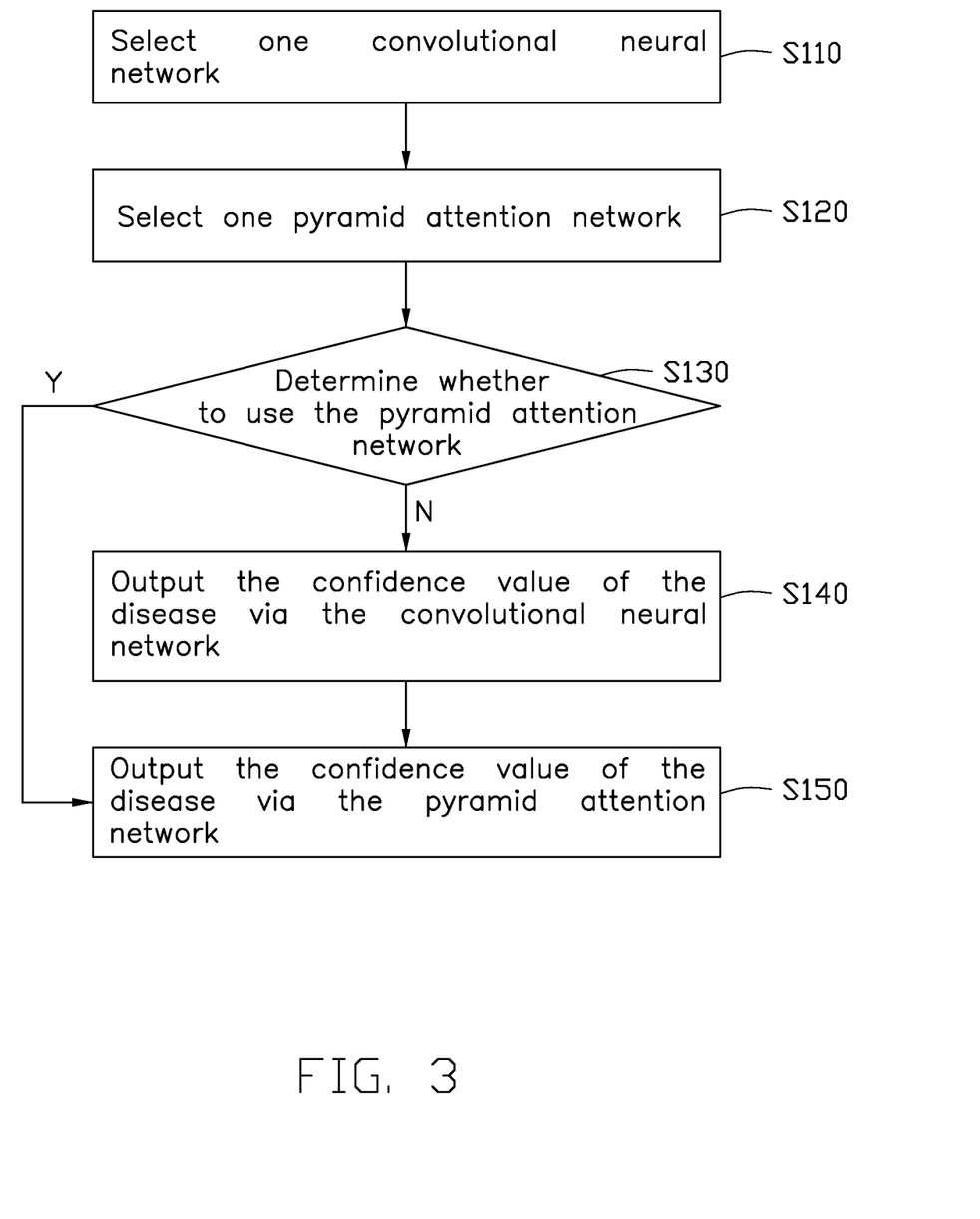
FIG. 3 is flowchart of a process for establishing a disease identifying model in the method.

FIG. 3 is flowchart of a process for establishing the disease identifying model in the method. As shown in the FIG. 3, the process for establishing the disease identifying model in the method of training disease identifying model can include:

At block S110, selecting one CNN.

In some embodiments, the CNN can be any one type of DenseNet, ResNeXt, InceptionNet, and SeNet. In some embodiments, the CNN can be BIG Transfer (BiT).

It can be understood that, after the selection of the type of the CNN, a quantity of layers of the CNN can be selected according to the feature maps and an amount of data. For example, when the disease identifying model is established based on the DenseNet, DenseNet121, DenseNet169, or DenseNet201 can be selected.

At step S120, selecting one pyramid attention network.

In some embodiments, the pyramid attention network can be any one of feature pyramid attention, path aggregation feature pyramid attention, bidirectional feature pyramid attention, and recursive feature pyramid attention. The levels in the pyramid attention network are connected via a fast normalized fusion technique.

It can be understood that, when the CNN can not correctly identify the lesion locations in the medical images, the pyramid attention network can be set in the disease identifying model, to improve the training effectively of the disease identifying model.

At step S130, determining whether to use the pyramid attention network.

In some embodiments, a set of data can be input into the disease identifying model to verify the disease identifying model. And the verification training result of the disease identifying model according to the step S400 can be used to determine whether the pyramid attention network needs to be used in the disease identifying model. If the pyramid attention network needs to be used in the disease identifying model, for example, if the CNN can not correctly identify the lesion locations in the medical images, the procedure goes to step S150. If the pyramid attention network does not need to be used in the disease identifying model, for example, if the CNN can correctly identify the lesion locations in the medical images, the procedure goes to step S140.

At step S140, outputting the confidence values of the diseases via the CNN.

In some embodiments, when the pyramid attention network does not need to be used in the disease identifying model, the disease identifying model does not include the pyramid attention network, and the confidence values of a variety of diseases are output via a preset function of the CNN.

It can be understood that, the preset function can be a sigmoid function. The sigmoid function is monotone increasing and its inverse is also monotone increasing. The sigmoid function can be used as an actvation function of the CNN and maps the variables to a range of 0 to 1. The sigmoid function can be used as a classifier, and the effect of the sigmoid function can be better when a different between the lesion features is complex or is not extremely large.

At step S150, outputting the confidence value of the disease via the pyramid attention network.

In some embodiments, when the pyramid attention network needs to be used in the disease identifying model, the disease identifying model includes the convolutional neural network and the pyramid attention network, and the output from the CNN can be input into the pyramid attention network, and the confidence values of a variety of diseases are output via the pyramid attention network.

Figure 4:
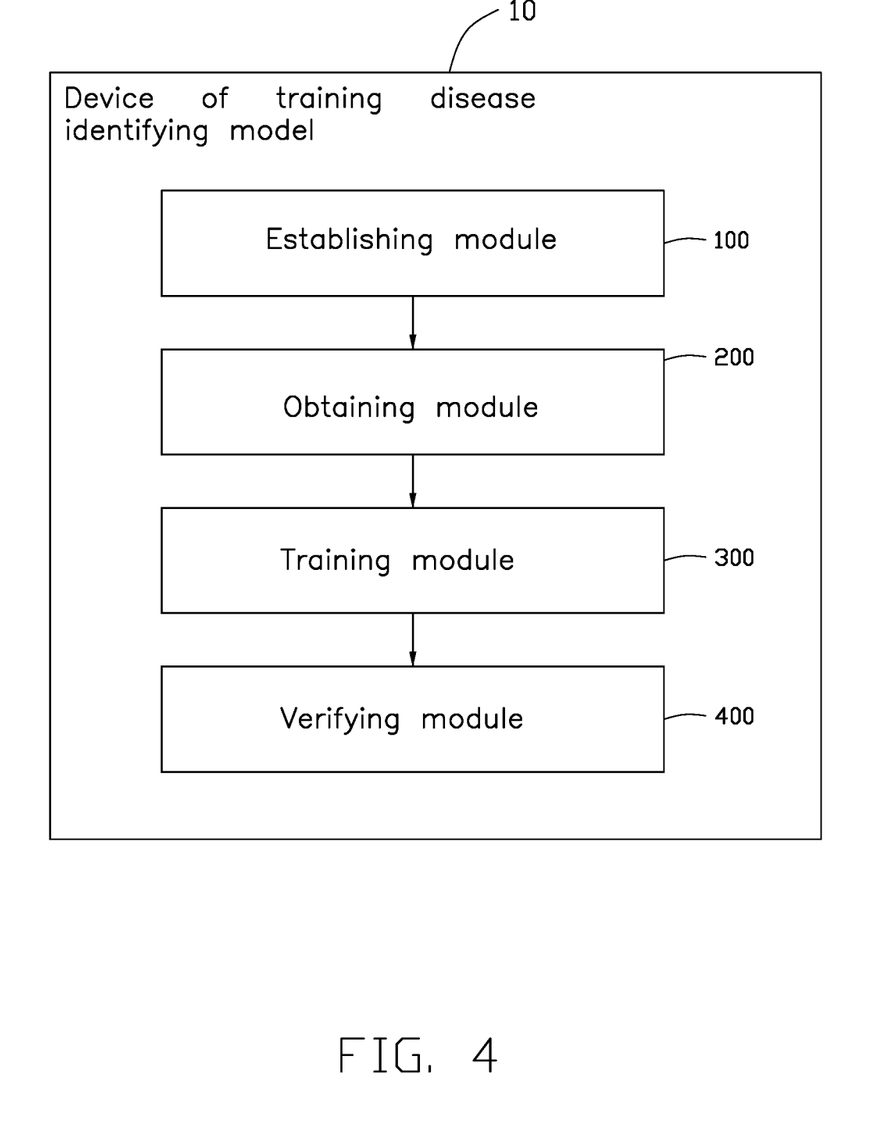
FIG. 4 is a block diagram of an embodiment of a device of training disease identifying model.

FIG. 4 is a block diagram of an embodiment of a device of training disease identifying model. The device of training disease identifying model can include an establishing module 100, an obtaining module 200, a training module 300, and a verifying module 400.

In some embodiments, the establishing module 100 can be configured to execute a step S100 of the FIG. 1 and a step S110-S150 of the FIG. 3 to establish a disease identifying model. The specific implementation solution refers to the FIG. 1, the FIG. 3, and correlation description.

In some embodiments, the obtaining module 200 can be configured to execute a step S200 of the FIG. 1 to obtain feature map sample set, the feature map sample set being classified into training sets and verification sets. The specific implementation solution refers to the FIG. 1 and correlation description.

In some embodiments, the training module 300 can be configured to execute a step S300 of the FIG. 1 to train the disease identifying model and perform a statistics to the output confidence values of the diseases and the disease identifying models, for verification and analysis the disease identifying models. The specific implementation solution refers to the FIG. 1, the FIG. 3, and correlation description.

In some embodiments, the verifying module 400 can be configured to execute a step S400 of the FIG. 1 to verify the disease identifying models via the feature maps in the verification sets and a preset classifier. The specific implementation solution refers to the FIG. 1 and correlation description.

Figure 5:
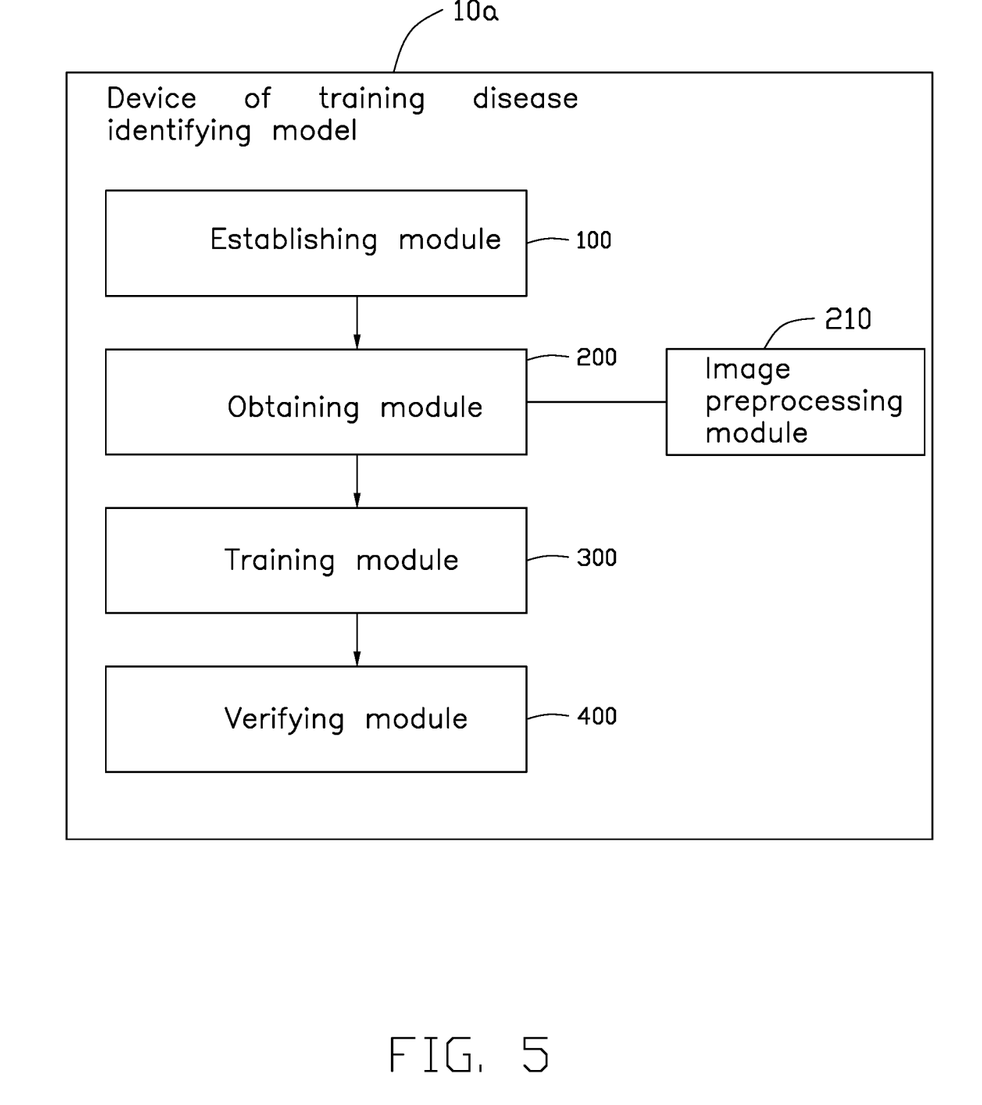
FIG. 5 is a block diagram of another embodiment of such a device.

FIG. 5 is a block diagram of another embodiment of a device of training disease identifying model. The device of training disease identifying module in the FIG. 5 is similar to the device of training disease identifying module in the FIG. 4. The difference between the device of training disease identifying module in the FIG. 5 and the device of training disease identifying module in the FIG. 4 is that, the device of training disease identifying model can further include an image preprocessing module 210.

In some embodiments, the image preprocessing module 210 can be configured to obtain a preset number of the medical images and preprocess the obtained preset number of the medical images to obtain the feature map sample set. The specific implementation solution refers to the FIG. 1, the FIG. 2, and correlation description.

In some embodiments, the device of training disease identifying model 10/10a, is capable of training the disease identifying model according to the medical images with different specification, and the trained disease identifying module can be adapted to different medical images and has a higher recognition rate.

In some embodiments, a non-transitory storage medium is provided. The non-transitory storage medium stores computer readable program code embodied thereon. The computer readable program code being executed by at least one processor of an electronic device, causing the at least one processor to execute the step S100-S400 of the method of training disease identifying model of the FIG. 1, the step S210-S300 of the method of training disease identifying model of the FIG. 2, and the step S110-S150 of the method of training disease identifying model of the FIG. 3.

The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing.

It should be emphasized that the above-described embodiments of the present disclosure, including any particular embodiments, are merely possible examples of implementations, set forth for a clear understanding of the principles of the disclosure. Many variations and modifications can be made to the above-described embodiment(s) of the disclosure without departing substantially from the spirit and principles of the disclosure. All such modifications and variations are intended to be included herein within the scope of this disclosure and protected by the following claims.

What is claimed is:

1. A method of training disease identifying model comprising:
   establishing a disease identifying model, the disease identifying model comprising a convolutional neural network and a pyramid attention network, the pyramid attention network being connected to an output of the convolutional neural network;
   obtaining feature map sample set, the feature map sample set being classified into one or more training sets and one or more verification sets;
   inputting each of the training sets into the disease identifying model to train the disease identifying model according to the one or more training sets and output values of degree of confidence in correct identification of diseases; and
   verifying the disease identifying models after being trained according to the one or more verification sets and the values of degree of confidence in correct identification of diseases;
   wherein the obtaining feature map sample set comprises:
   obtaining a preset number of the medical images; and
   preprocessing the obtained preset number of the medical images to obtain the feature map sample set;
   wherein the preprocessing the obtained preset number of the medical images to obtain the feature map sample set comprises:
   resampling the medical images;
   converting the medical images after resampling to three-dimensional RGB images;
   converting the three-dimensional RGB images into the feature maps of the medical images.

2. The method according to claim 1, wherein the converting the three-dimensional RGB images into the feature maps of the medical images comprises:
   mean normalizing the converted three-dimensional RGB images;
   performing an image enhancement on the three-dimensional RGB image after the mean normalization, to convert to the feature maps of the medical images.

3. The method according to claim 1, wherein:
   the establishing the disease identifying model comprises:
   selecting one convolutional neural network;
   selecting one pyramid attention network;
   wherein the disease identifying model comprising the convolutional neural network and the pyramid attention network comprises:
   the disease identifying model comprising the convolutional neural network and the pyramid attention network if the pyramid attention network needs to be used in the disease identifying model;
   outputting values of degree of confidence in correct identification of diseases comprises:
   outputting the values of degree of confidence in correct identification of diseases via the pyramid attention network.

4. The method according to claim 3, wherein the method further includes:
   outputting the values of degree of confidence in correct identification of diseases via a preset function of the convolutional neural network if the pyramid attention network does not need to be used in the disease identifying model.

5. The method according to claim 4, wherein the method further includes:
    determining whether the value of degree of confidence in correct identification of disease is greater than a preset threshold;
    outputting the disease corresponding to the value of degree of confidence in correct identification of disease if the value of degree of confidence in correct identification of disease is greater than the prese threshold.

6. An electronic device comprising:
    a storage device;
    at least one processor; and
    the storage device storing one or more programs, which when executed by the at least one processor, cause the at least one processor to:
    establish a disease identifying model, the disease identifying model comprising a convolutional neural network and a pyramid attention network, the pyramid attention network being connected to an output of the convolutional neural network;
    obtain feature map sample set, the feature map sample set being classified into one or more training sets and one or more verification sets;
    input each of the training sets into the disease identifying model to train the disease identifying model according to the one or more training sets and output values of degree of confidence in correct identification of diseases; and
    verify the disease identifying models after being trained according to the one or more verification sets and the values of degree of confidence in correct identification of diseases;
    obtain a preset number of the medical images; and
    preprocess the obtained preset number of the medical images to obtain the feature map sample set;
    resample the medical images;
    convert the medical images after resampling to three-dimensional RGB images;
    convert the three-dimensional RGB images into the feature maps of the medical images.

7. The electronic device according to claim 6, further causing the at least one processor to:
    mean normalize the converted three-dimensional RGB images;
    perform an image enhancement on the three-dimensional RGB image after the mean normalization, to convert to the feature maps of the medical images.

8. The electronic device according to claim 6, further causing the at least one processor to:
    select one convolutional neural network;
    select one pyramid attention network; where the disease identifying model comprising the convolutional neural network and the pyramid attention network if the pyramid attention network needs to be used in the disease identifying model;
    output the values of degree of confidence in correct identification of diseases via the pyramid attention network.

9. The electronic device according to claim 8, further causing the at least one processor to:
    output the values of degree of confidence in correct identification of diseases via a preset function of the convolutional neural network if the pyramid attention network does not need to be used in the disease identifying model.

10. The electronic device according to claim 9, further causing the at least one processor to:
    determine whether the values of degree of confidence in correct identification of disease is greater than a preset threshold;
    output the disease corresponding to the values of degree of confidence in correct identification of disease if the values of degree of confidence in correct identification of the disease is greater than the prese threshold.

11. A non-transitory storage medium storing a set of commands, when the commands being executed by at least one processor of an electronic device, causing the at least one processor to:
    establish a disease identifying model, the disease identifying model comprising a convolutional neural network and a pyramid attention network, the pyramid attention network being connected to an output of the convolutional neural network;
    obtain feature map sample set, the feature map sample set being classified into one or more training sets and one or more verification sets;
    input each of the training sets into the disease identifying model to train the disease identifying model according to the one or more training sets and output values of degree of confidence in correct identification of the diseases; and
    verify the disease identifying models after being trained according to the one or more verification sets and the values of degree of confidence in correct identification of diseases;
    obtain a preset number of the medical images; and
    preprocess the obtained preset number of the medical images to obtain the feature map sample set;
    resample the medical images;
    convert the medical images after resampling to three-dimensional RGB images;
    convert the three-dimensional RGB images into the feature maps of the medical images.

12. The non-transitory storage medium according to claim 11, further causing the at least one processor to:
    select one convolutional neural network;
    select one pyramid attention network; where the disease identifying model comprising the convolutional neural network and the pyramid attention network if the pyramid attention network needs to be used in the disease identifying model;
    output the values of degree of confidence in correct identification of diseases via the pyramid attention network.

13. The non-transitory storage medium according to claim 12, further causing the at least one processor to:
    output the values of degree of confidence in correct identification of disease via a preset function of the convolutional neural network if the pyramid attention network does not need to be used in the disease identifying model.

14. The non-transitory storage medium according to claim 13, further causing the at least one processor to:
    determine whether the value of degree of confidence in correct identification of disease is greater than a preset threshold;
    output the disease corresponding to the value of degree of confidence in correct identification of disease if the value of degree of confidence in correct identification of disease is greater than the prese threshold.

* * * * *